(12) United States Patent
Sawyers

(10) Patent No.: US 6,973,822 B1
(45) Date of Patent: Dec. 13, 2005

(54) SAFETY DRIVE HAMMER FOR A DYNAMIC CONE PENETROMETER

(76) Inventor: J. Michael Sawyers, 1900 Mountain Rd., Haymarket, VA (US) 20169-1349

( * ) Notice: Subject to any disclaimer, the term of this patent is extended or adjusted under 35 U.S.C. 154(b) by 780 days.

(21) Appl. No.: 09/789,758

(22) Filed: Feb. 22, 2001

Related U.S. Application Data

(60) Provisional application No. 60/183,753, filed on Feb. 22, 2000.

(51) Int. Cl.$^7$ .............................................. G01N 3/42
(52) U.S. Cl. .............................................. 73/82; 73/84
(58) Field of Search ................ 73/78, 81, 82, 73/84; 173/70, 90

(56) References Cited

U.S. PATENT DOCUMENTS

| | | |
|---|---|---|
| 3,080,749 A | 3/1963 | Hollander |
| 3,331,240 A | 7/1967 | Nilsson et al. |
| 3,625,295 A * | 12/1971 | Gunning ..................... 173/135 |
| 4,405,020 A | 9/1983 | Rassieur |
| 5,313,825 A | 5/1994 | Webster et al. |
| 5,616,833 A | 4/1997 | Andersson |
| 5,663,649 A | 9/1997 | Topp et al. |
| 5,886,253 A | 3/1999 | Joustra |
| 6,138,501 A * | 10/2000 | Rastegar ......................... 73/82 |

FOREIGN PATENT DOCUMENTS

| | | | | |
|---|---|---|---|---|
| GB | 1420747 | * | 1/1976 | ..................... 73/84 |
| JP | 207513 | * | 8/1989 | ..................... 73/84 |

* cited by examiner

*Primary Examiner*—Hezron Williams
*Assistant Examiner*—Nashmiya Fayyaz
(74) *Attorney, Agent, or Firm*—James Creighton Wray; Meera P. Narasimhan

(57) ABSTRACT

Drive hammer assembly with a drive hammer and rod is used with dynamic cone penetrometer tests. A rod end is attached to a cone penetrometer used to measure strength and density of soil. The assembly has no exterior impact zones, eliminating any chance of user injury. A casing loosely fits around a rod. A casing upper end is fitted with a top plate and lower end is fitted with an end plate through which the rod passes. Upper end of the rod is flared with a shoulder which may be welded to the top of the rod. Lower end of the rod is threaded to connect the rod to standard rod and cone assemblies. The hammer is raised to the shoulder on the upper end of the rod. The hammer slides along the rod until the top plate impacts upon the shoulder and drives the DCP cone into the ground.

34 Claims, 5 Drawing Sheets

SAFETY HAMMER ASSEMBLY

SAFETY HAMMER CUTAWAY VIEW

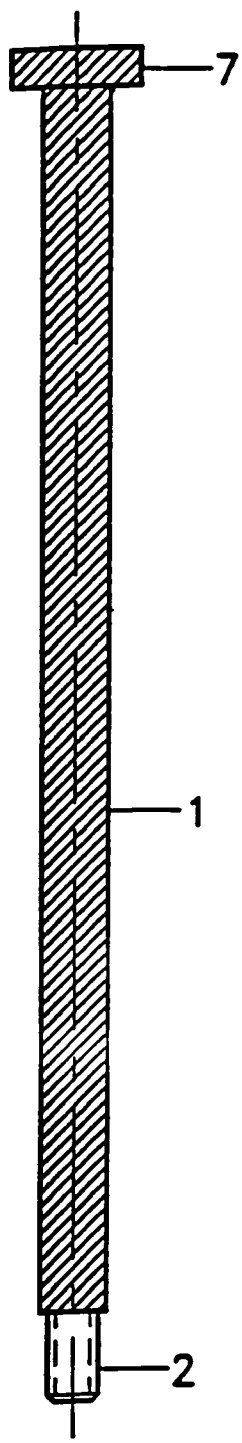
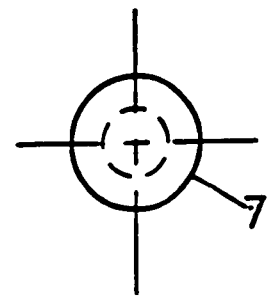
TOP VIEW - DRILL ROD
FIG. 3B
SIDE VIEW OF E - DRILL ROD
FIG. 3A

SECTION – DRIVE HAMMER

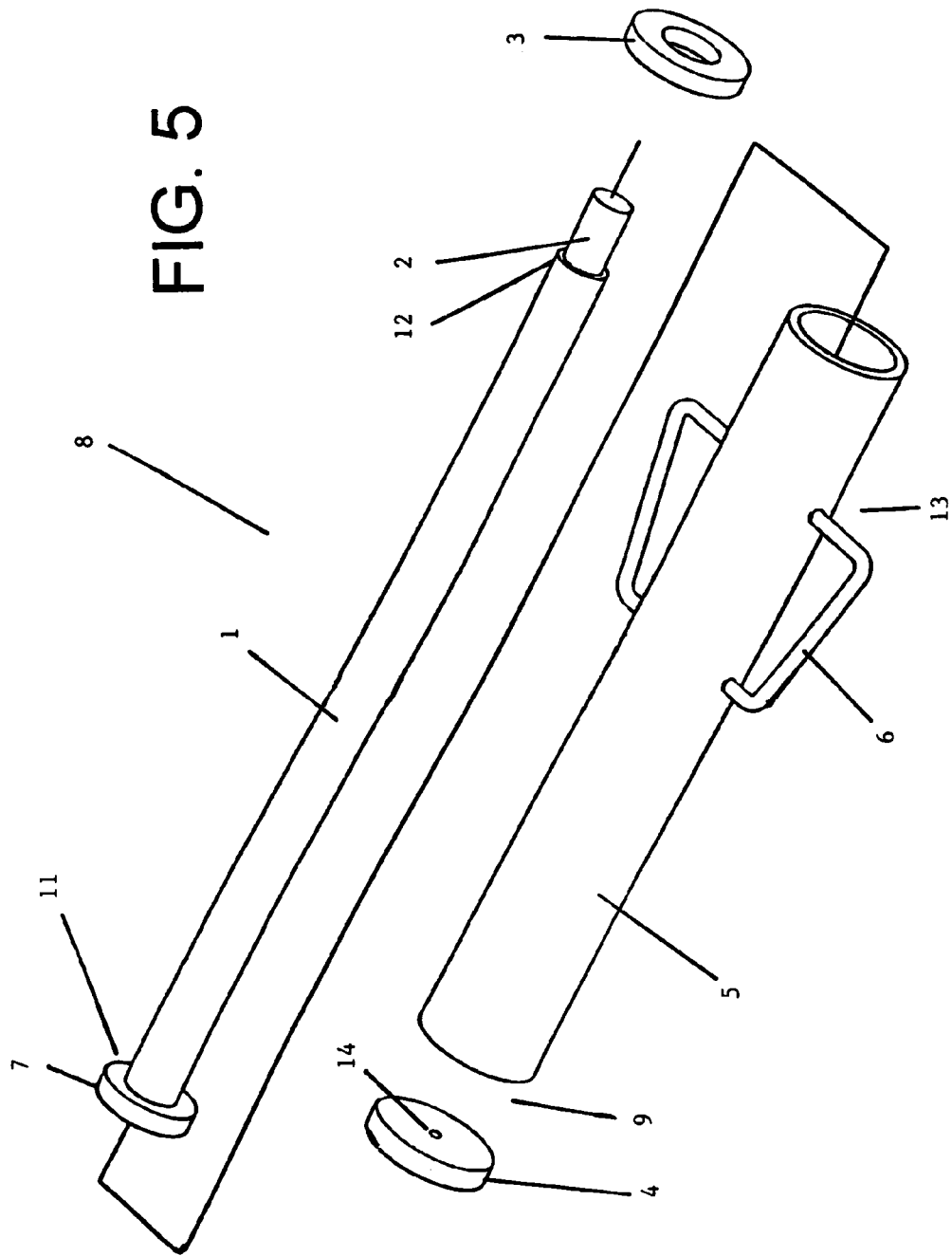

SAFETY DRIVE HAMMER FOR A DYNAMIC CONE PENETROMETER

This application claims the benefit of U.S. Provisional Application Ser. No. 60/183,753, filed Feb. 22, 2000.

BACKGROUND OF THE INVENTION

Soil must be tested prior to beginning any construction to ascertain the strength and the density of the soil. One method of testing the strength and the density of soil is with a dynamic cone penetrometer (DCP). The DCP testing method has been standardized by the American Society for Testing and Materials in Special Technical Publication #399 (ASTM STP-399).

Existing DCP's comprise a fifteen pound steel plate (hammer) that is slidably mounted on a steel rod, typically an "E drill" rod. The upper end of the rod is fitted with a first stationary steel ring. A second steel ring is mounted on the rod approximately twenty inches below the first steel ring. The hammer is lifted up to the upper ring and permitted to drop a height of twenty inches, at which point it impacts the lower ring, thereby driving the penetrating cone of the DCP deeper into the ground. The number of impacts required to move the cone a predetermined distance into the ground becomes an index of the strength and the density of the soil.

One problem with existing DCP's is that the two impact zones (the upper and lower steel rings that are the boundaries of the steel hammer's movement along the rod) are exposed. A user often injures a finger or a hand by catching it in the line of travel of the steel hammer during use of the DCP. A user may also be hurt by the movement of the steel hammer along the rod while transporting the DCP.

A need exists for a dynamic cone penetrometer that eliminates the potential for injuries to users while using and carrying the DCP.

SUMMARY OF THE INVENTION

The present invention is a drive hammer used in performance of the dynamic cone penetrometer (DCP) test in accordance with ASTM STP-399. The DCP is a mechanical device comprising a drive hammer assembly and a rod that is equipped with a cone penetrometer that is used to measure the strength and the density of soil.

The DCP hammer of the present invention is capable of satisfying the standard "weight and drop height" requirements of the ASTM standard. However, the present DCP drive hammer differs from existing DCP drive hammers in that there are no exterior impact zones, thereby providing a DCP that is much safer to use. The impact zones of the present invention are completely interior, minimizing or eliminating any chance that a user may injure himself while using the DCP.

The preferred safety drive hammer assembly has a drive hammer and a rod. The rod has an end for attachment to a standard rod or dynamic cone penetrometer. The drive hammer assembly of the present invention has impact zones that are completely interior, eliminating any chance of user injury.

The upper end of the casing has a top plate, which is preferably solid steel, and the lower end has an end plate through which the rod passes. The end plate is preferably solid steel.

Plates may be attached by any known means to the cylindrical casing. For example, but not limited to, the end plate may be threaded on threads at an end of the casing, or attached by axial tapped screws, or the like.

The upper end of the rod is preferably flared with a shoulder, which is preferably a solid steel cap. The shoulder may be welded to the top of the rod. The lower end of the rod is threaded to match standard DCP "E drill" rod extensions. This allows the hammer assembly to be connected to standard rod and cone assemblies.

In preferred embodiments, when the hammer is raised to the shoulder, the end plate abuts the shoulder. When the hammer is dropped, it slides along the rod until the top plate impacts upon the shoulder at the upper end of the rod. The impact upon the shoulder drives the cone of the DCP into the ground. Generally, a predetermined distance is marked several times along the length of the DCP rods attached to end of rod, the first mark being flush with the ground. Soil strength and density may be calculated based upon how many drops of the hammer it takes to move the DCP that predetermined distance into the ground.

Preferably, handles may be fitted to the casing to improve portability without injuring the user during usage and transportation of a DCP. The casing end plate, and/or the top plate, may be bolted to the casing to permit periodic inspection, cleaning and maintenance of the interior of the drive hammer assembly.

These and further and other objects and features of the invention are apparent in the disclosure, which includes the above and ongoing written specification, with the claims and the drawings.

BRIEF DESCRIPTION OF THE DRAWINGS

FIGS. 1 and 5 are expanded views of the safety drive hammer assembly for a dynamic cone penetrometer.

FIGS. 3A and 3B are respectively side and top views showing the drill rod for the safety drive hammer assembly.

DETAILED DESCRIPTION OF THE PREFERRED EMBODIMENTS

Figure 1:
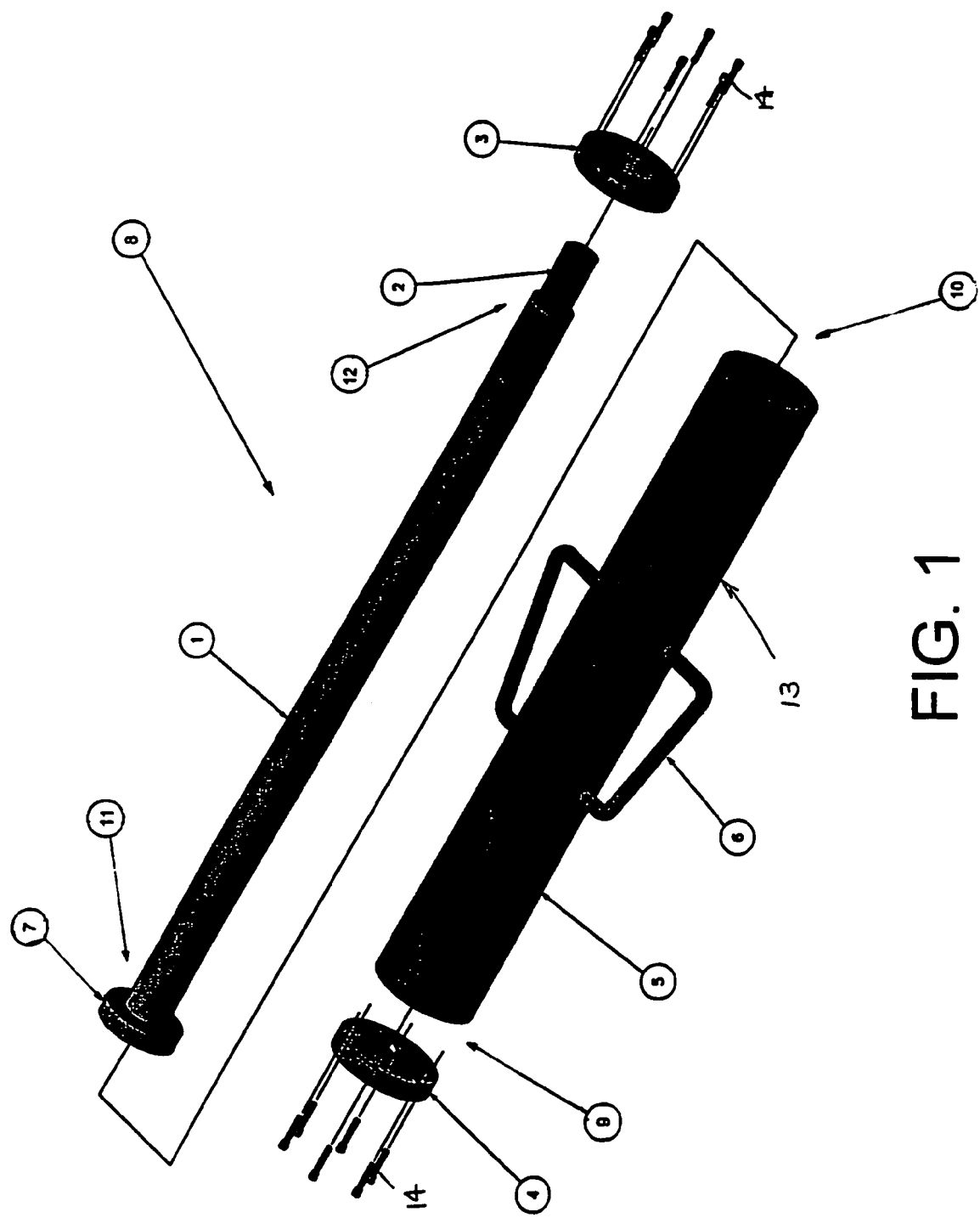
Figure 2:
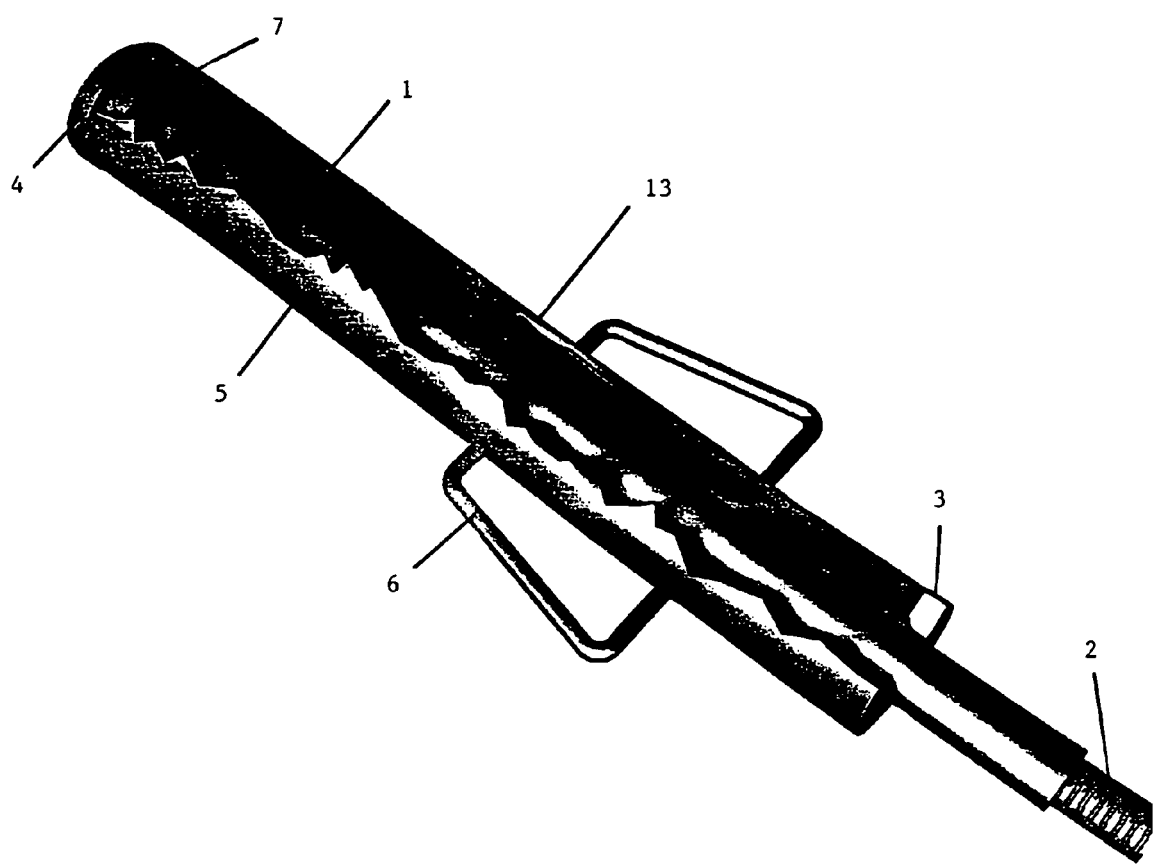
FIG. 2 is a partial sectional perspective view of the safety drive hammer assembly for a dynamic cone penetrometer with a view of the internals of the hammer assembly.
Figure 4:
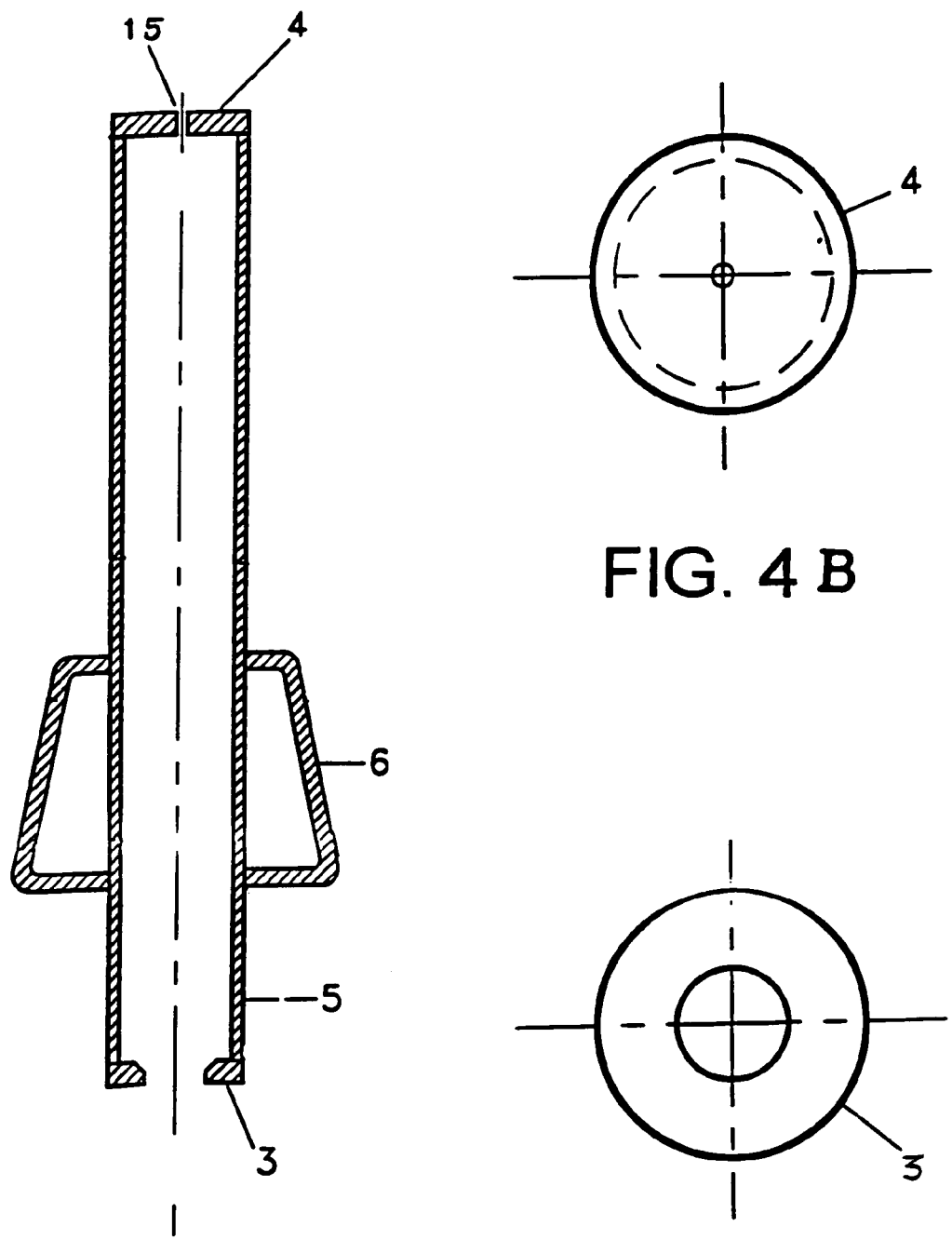
FIGS. 4A, 4B, and 4C are respectively sectional, top and bottom views showing the hammer for the safety drive hammer assembly.

As shown in FIGS. 1–5, the present invention is a drive hammer assembly 8 used in performance of the dynamic cone penetrometer (DCP) test in accordance with ASTM STP-399.

In FIGS. 1–5, the safety drive hammer assembly 8 is a mechanical device comprising a drive hammer 13 and a rod 1. The rod 1 has an end 2 for attachment to a cone penetrometer that is used to measure the strength and the density of soil. The drive hammer assembly of the present invention is capable of satisfying the standard "weight and drop height" requirements of the ASTM standard. However, the present drive hammer differs from that of existing DCP's in that there are no exterior impact zones, thereby providing a DCP that is much safer to use. The impact zones of the present invention are completely interior, eliminating any chance that a user may injure himself while using the DCP. The dimensions for each of the elements of the invention detailed in this application are merely exemplary of, and inclusive but not limited to, the different ranges of dimensions within the scope of this invention.

The drive hammer assembly 8 includes a casing 5 that is loosely fitted around a rod 1. The casing 5 is a 0.250 inch, preferably, but not limited to, a 0.218 inch, thick steel tube that is, for example, approximately 20.5 inches, preferably, but not limited to, 22 inches, long with an outer diameter of, for example, approximately 3 inches, preferably, but not limited to, 2.375 inches. The rod 1 is preferably of any metal, such as a solid steel rod or, for example, an approximately 0.25 inch thick steel tube that is, for example, approximately 24 inches, preferably, but not limited to, 28 inches, long with an outer diameter of, for example, approximately 1 5/16 inches, preferably, but not limited to, 1.315 inches.

As seen in FIGS. 1–5, the upper end 9 of the casing 5 is fitted with a top plate 4, which is preferably, but not limited to, solid steel and has a thickness of, for example, approximately 0.5 inches, preferably, but not limited to, 2 inches, and an axially punched opening 15 is, for example, approximately 0.25 inches in diameter. The lower end 10 of the casing 5 is fitted with an end plate 3 through which the rod 1 passes. The end plate 3 is preferably solid steel and, for example, approximately 0.5 inches, preferably, but not limited to, 2 inches thick.

Plates 3 and/or 4 may be attached with cap screws 14 received in axial tapped holes at the ends of the cylindrical casing 5. Also, plates 3 and/or 4 may be attached to the ends of the cylindrical casing 5 by welding. The end plate 3 may be threaded on threads at an end of the casing. Also, end plate 3 may be attached by axial tapped screws 14.

As seen in FIGS. 1–5, the upper end 11 of the rod 1 is flared with a shoulder 7, which is preferably a solid steel cap that is, for example, approximately 0.5 inches, preferably, but not limited to, 2 inches, thick with a diameter of, for example, approximately 2 5/16 inches, preferably, but not limited to, 1.9 inches. The shoulder 7 may be welded to the top of the rod 1. The lower end 12 of the rod 1 is threaded 2 to match standard DCP "E drill" rod extensions. This allows the hammer assembly 8 to be connected to standard rod and cone assemblies.

The hammer 13 is raised to the shoulder 7 on the upper end of the rod 1, with the end plate 3 touching the shoulder 7. When the hammer 13 is dropped, it slides along the rod 1 until the top plate 4 impacts upon the shoulder 7 at the upper end of the rod 1. The impact upon the shoulder 7 drives the cone of the DCP into the ground. Generally, a predetermined distance is marked several times along the length of the DCP rods attached to end 2 of rod 1, the first mark being flush with the ground. Soil strength and density may be calculated based upon how many drops of the hammer it takes to move the DCP that predetermined distance into the ground.

Two handles 6 may be fitted to the exterior of the casing 5 to facilitate usage and carrying of the hammer assembly. This feature prevents the existing problem of injuries received during usage and transportation of a DCP.

The casing end plate 3, and/or the top plate 4, may be bolted to the casing 5 to permit periodic inspection, cleaning and maintenance of the interior of the drive hammer assembly 8. The weight of the drive hammer assembly 8 is, for example, approximately thirty pounds, preferably, but not limited to, twenty pounds. The preferred drop hammer 13 has, for example, a fifteen pound drop weight. The hammer weight consists of the casing 5, top plate 4, end plate 3, and handles 6, and if present, screws 14. The drill rod assembly weighs, for example, approximately fifteen pounds, preferably, but not limited to five pounds, consisting of the rod 1, shoulder 7 and thread end 2. The drive hammer assembly 8 allows for obtaining the standard drop height of twenty inches, as set forth in ASTM STP-399.

While the invention has been described with reference to specific embodiments, modifications and variations of the invention may be constructed without departing from the scope of the invention, which is defined in the following claims.

I claim:

1. A drop hammer apparatus comprising a drop hammer assembly, a rod partially disposed coaxially within an interior of the drop hammer assembly, and two impact zones of the drop hammer assembly and the rod on an interior of the drop hammer assembly, wherein the drop hammer assembly comprises a casing movably disposed around the rod, and first and second ends on the casing, a top plate on the first end of the casing, an end plate on the second end of the casing, wherein the rod passes through the end plate, wherein the rod further comprises upper and lower ends, and a solid steel cap on the upper end, wherein the cap on the upper end of the rod restricts movement of the end plate along the rod when the hammer is raised, and wherein the cap receives an impact of the top plate at the upper end of the rod when the hammer assembly is dropped for driving a cone of a penetrometer into ground.

2. The apparatus of claim 1, wherein the drive hammer assembly obtains a standard drop height of about twenty inches.

3. The apparatus of claim 1, wherein the casing is a cylindrical tube of metal.

4. The apparatus of claim 3, wherein the metal is steel.

5. The apparatus of claim 4, wherein the tube has a thickness of about 0.218 inches.

6. The apparatus of claim 4, wherein the tube has a length of about 22 inches.

7. The apparatus of claim 4, wherein the tube has an outer diameter of about 2.375 inches.

8. The apparatus of claim 1, wherein the rod is a tube of metal.

9. The apparatus of claim 8, wherein the metal is steel.

10. The apparatus of claim 8, wherein the tube has a thickness of about 0.25 inches.

11. The apparatus of claim 8, wherein the tube has a length of about 28 inches.

12. The apparatus of claim 8, wherein the tube has an outer diameter of about 1.315 inches.

13. The apparatus of claim 1, wherein the rod has a weight of about five pounds.

14. The apparatus of claim 1, wherein the top plate is of solid metal.

15. The apparatus of claim 14, wherein the metal is steel.

16. The apparatus of claim 1, wherein the top plate has a thickness of about 2 inches.

17. The apparatus of claim 1, wherein the top plate further comprises an axial opening.

18. The apparatus of claim 17, wherein the opening has a diameter of about 0.25 inches.

19. The apparatus of claim 1, wherein the drive hammer assembly has a weight of about twenty pounds.

20. The apparatus of claim 1, wherein the hammer has a drop weight of about fifteen pounds.

21. The apparatus of claim 1, wherein the end plate is of solid steel.

22. The apparatus of claim 1, wherein the end plate has a thickness of about 2 inches.

23. The apparatus of claim 1, wherein the top plate is attached to the first end of the casing by welding.

24. The apparatus of claim 1, wherein the end plate is attached to the second end of the casing by welding.

25. The apparatus of claim 1, wherein the lower end has connectors for connecting to a cone or a rod penetrometer assembly.

26. The apparatus of claim 1, further comprising axial tapped screws and openings in the end plate for receiving the screws and for attaching the end plate to the second end of the casing.

27. The apparatus of claim 1, wherein the penetrometer has markings corresponding to predetermined distances for indicating soil properties proportional to a force and to a number of impacts of the hammer for moving the penetrometer into the ground over each marking.

28. The apparatus of claim 1, further comprising at lest two handles on an exterior of the casing for facilitating portability of the hammer assembly.

29. The apparatus of claim 1, wherein the end plate is removably connected to the casing.

30. The apparatus of claim 1, wherein the upper end has a thickness of about 2 inches.

31. The apparatus of claim 1, wherein the upper end has a diameter of about 1.9 inches.

32. The apparatus of claim 1, wherein the shoulder is welded to the rod.

33. The apparatus of claim 25, wherein the shoulder on the upper end of the rod restricts movement of the end plate along the rod when the hammer is raised.

34. The apparatus of claim 25, wherein the connectors are threads for connecting to complementary threading on the penetrometer assembly.

* * * * *